United States Patent [19]

Drury et al.

[11] Patent Number: 4,474,959

[45] Date of Patent: Oct. 2, 1984

[54] PRODUCTION OF FORMATE SALTS FROM CARBON DIOXIDE, HYDROGEN AND AMINES

[75] Inventors: David J. Drury; John E. Hamlin, both of Hull, England

[73] Assignee: BP Chemicals Limited, London, England

[21] Appl. No.: 494,640

[22] Filed: May 16, 1983

[30] Foreign Application Priority Data

May 22, 1982 [GB] United Kingdom ............... 8215015

[51] Int. Cl.$^3$ .................... C07C 53/06; C07C 51/15; C07D 487/08; C07D 213/18
[52] U.S. Cl. ................................ 544/351; 260/243.3; 260/501.1; 546/348; 562/609; 562/550
[58] Field of Search .................... 544/351; 260/501.1; 260/243.3; 562/550

[56] References Cited

PUBLICATIONS

Inoue et al., J. Chem. Soc. Commun., 17, 718, (1975).
Inoue et al., Chem. Abs., 87, 67853, (1977).
Inoue et al., Chem. Lett., 8, 863–864, (1976).

Primary Examiner—Mark L. Berch
Attorney, Agent, or Firm—Brooks, Haidt, Haffner & Delahunty

[57] ABSTRACT

Formate salts of nitrogenous bases containing tertiary nitrogen are prepared by reacting the nitrogenous base with carbon dioxide and hydrogen using a soluble transition metal catalyst. For example triethylamine is reacted with carbon dioxide and hydrogen using ruthenium trichloride as catalyst and an isopropanol/water mixture as solvent to yield triethylammonium formate which was separated from the reaction mixture by distillation.

17 Claims, No Drawings

PRODUCTION OF FORMATE SALTS FROM CARBON DIOXIDE, HYDROGEN AND AMINES

The present invention relates to a process for the production of formate salts of nitrogenous bases containing tertiary nitrogen atoms.

Trialkylammonium formates have been used in the reduction of carbonyl compounds (Kataoka, Shinji; Tabata, Masayoshi; Takata, Yoshiyuki; Hokkaido Daigaku Kogakubu Kenkyu 1972, (63), 145–51 (Japan), as catalysts in the production of monoalkyl ethers of trimethyleneglycol (USSR Pat. No. 495300), and in the production of polyurethane foams from resole polyols (U.S. Pat. No. 4,293,658) and in various other applications. They are generally produced by reacting formic acid with the appropriate tertiary amine.

Japanese patent publication No. 53-46820 describes the production of formic acid and its esters by reacting a compound of formula ROH (wherein R is either hydrogen or a hydrocarbon group) with carbon dioxide and hydrogen in the presence as catalyst of low valent and/or hydride complexes of Group VIII transition metals and basic materials containing alkali metals and alkaline earth metals. The specification teaches that using water as solvent the product is formic acid and using an alkanol as solvent the product is an ester of formic acid.

Japanese patent publication No. 53-46816 describes the production of formic acid and its esters by a similar reaction to that described in publication No. 53-46820 except that instead of an inorganic base there is employed an organic base which is an aliphatic tertiary amine.

Finally, Japanese patent publication No. 53-46818 describes the production of alkali metal formates by reacting alkali metal carbonates with carbon dioxide and hydrogen.

We have now found that formate salts of nitrogenous bases containing tertiary nitrogen atoms can be produced by reacting carbon dioxide and hydrogen in the presence of the base in alcoholic or aqueous alcoholic media using as catalyst a compound of a transition metal of Group VIII of the Periodic Table according to Mendeleef.

Accordingly, the present invention provides a process for the production of a formate salt of a nitrogenous base containing a tertiary nitrogen atom which process comprises reacting hydrogen and carbon dioxide with the nitrogenous base, in the presence of a solvent and as catalyst a soluble compound of a transition metal of Group VIII of the Periodic Table according to Mendeleef and separating the formate salt of the base from the reaction mixture.

The carbon dioxide may either be carbon dioxide itself, which is widely available on an industrial scale, or a carbonate or a bicarbonate or a mixture thereof. Carbon dioxide may be used as a gas or as a liquid or as a solid, preferably as a gas. Using carbon dioxide gas as the source of carbon dioxide it is preferred to use partial pressures of carbon dioxide and hydrogen which are as high as is practicable and economic. The use of high partial pressures of hydrogen is desirable because the reaction rate and yield of the formate salt increase as the partial pressure increases. The partial pressure of carbon dioxide is less critical but suitably the carbon dioxide partial pressure may be up to 60 bar and the hydrogen partial pressure up to 250 bar.

Conveniently the partial pressure of carbon dioxide is from 10 to 50 bar and that of hydrogen from 10 to 150 bar. The ratio of the partial pressure of hydrogen to that of carbon dioxide is preferably at least 1:1 more preferably at least 1.5:1.

The nitrogenous base containing a tertiary nitrogen atom may suitably be of formula:

or of formula:

wherein in the formulae, $R^1$, $R^2$ and $R^3$, which may be the same or different, are hydrocarbyl groups or substituted hydrocarbyl groups or any two or all of $R^1$, $R^2$ and $R^3$ may form part of a ring, $R^4$ is a hydrocarbyl group or substituted hydrocarbyl group and $R^5$ is a divalent organic group or $R^4$ and $R^5$ may form part of a ring. Suitably the hydrocarbyl group is an aliphatic, cycloaliphatic, aryl or alkaryl group. Substituted hydrocarbyl groups may contain for example nitrogen or oxygen. Preferably the organic base is a trialkylamine, even more preferably a lower trialkylamine, for example a $C_1$ to $C_{10}$ trialkylamine. Examples of suitable trialkylamines are trimethylamine, triethylamine, tripropylamine and tributylamine. Examples of other nitrogenous bases which may be employed are 1,8-diazobicyclo[5.4.0]undec-7-ene (DBU) and 1,4-diazobicyclo[2.2.2]octane (DABCO), pyridine and picolines. Mixtures of nitrogenous bases may be used if so desired. Suitably the nitrogenous base concentration may be from 1 to 50% molar. The formate salt produced by the process corresponds to the nitrogenous base used as feed, for example using triethylamine the product is triethylammonium formate.

As solvent there may be used either one or more alcohols or a mixture of one or more alcohols with water. Suitable alcohols include methanol, ethanol, propanols and butanols. We have found that using secondary alcohol/water mixture a product consisting substantially exclusively of the formate salt can be produced whereas using other alcohols and alcohol/water mixtures there may be produced, in addition to the formate salt, formate esters. Of the secondary alcohol/water mixtures the use of isopropanol/water mixtures can lead to advantages in terms of rate and yields. It is therefore preferred to use as the solvent a mixture of isopropanol and water. Preferably isopropanol comprises from 30 to 90, even more preferably from 50 to 70, mole percent of the isopropanol/water mixture.

As catalyst there is used a compound of a Group VIII transition metal, which is preferably either iron, nickel, ruthenium, rhodium, palladium, iridium or platinum. More preferably the metal is ruthenium. Mixtures of compounds of different transition metals may also be used if so desired. The metal or metals may be added in any convenient form which is soluble in the reaction mixture. Thus the metal or metals may be added in the form of a simple salt, for example a halide, or in the form of a complex, for example a hydride complex. Examples of suitable ruthenium compounds which may be employed as catalyst are $RuCl_2(PPh_3)_3$, $RuH_2(PPh_3)_4$, $RuHCl(PPh_3)_4$, $RuCl_3.3H_2O$, $[Ru(CO)_2Cl_2]_n$, $[Ru(CO)_2I_2]_2$, $[(p\text{-cymene})RuCl_2]_2$, $[(hexamethylbenzene)RuCl_2]_2$ and $[(hexamethylbenzene)Ru_2(OH)_3]Cl$ and $Ru_3CO_{12}$. Suitably the catalyst concentration may be in the range 50 to 5000, preferably from 250 to 1000 parts per million by weight.

The process may suitably be operated at a temperature in the range from 20° to 200°, preferably from 60° to 130° C.

The process may be carried out batchwise or continuously.

The invention will now be illustrated by reference to the following Examples. In these Examples the rate of reaction refers to the rate of production of the formate salt (moles/h) divided by the weight of the reaction solution (kgs). The conversion to formate salt was calculated according to either the following equations:

$$\frac{\text{moles of formate produced}}{\text{moles of nitrogenous base added}} \times 100\%$$

$$\frac{\text{moles of gas absorbed in the course of the reaction}}{\text{moles of nitrogenous base added} \times 2} \times 100\%$$

After many of the experiments a sample of the reaction discharge was taken, hydrolysed with 5N hydrochloric acid and analysed by gas-liquid chromatography for formic acid. The amount of formic acid found corresponded well with that expected from the gas absorption data.

EXAMPLE 1

Into an autoclave of 100 ml capacity made of stainless steel and fitted with a rotary stirrer were charged 14.7 g triethylamine, 38.0 g isopropanol, 7.4 g water and 0.06 g ruthenium trichloride trihydrate. The isopropanol water mixture formed a solvent for the catalyst and the triethylamine. The autoclave was closed and carbon dioxide was introduced until a steady pressure of 27 bar was obtained. Hydrogen was added to give a total pressure of 82 bar and the autoclave heated to 80° C. The rate of reaction was 1.6 mol kg$^{-1}$h$^{-1}$ with an overall conversion to product shown to be triethylammonium formate of 49.3% by infra red spectroscopy followed by hydrolysis followed by gas-liquid chromatography. The triethylammonium formate was separated from the reaction mixture by distillation in a 20 plate Oldershaw column. Two major fractions were collected, the first (77°–81° C. head temperature/760 mm mercury) consisted of isopropanol, water and triethylamine, the second distilled at 108°–110° C. head temperature/100 mm mercury to give the 1:3 amine:formic acid adduct.

EXAMPLE 2

Into an autoclave similar to that described in Example 1 except of 300 ml capacity were charged 28.2 g triethylamine, 101.2 g isopropanol, 19.6 g water and 0.137 g $[Ru(CO)_2Cl_2]_n$. As in Example 1 the triethylamine and the ruthenium catalyst dissolved in the mixture of isopropanol and water. The autoclave was closed and carbon dioxide was introduced until a steady pressure of 27 bars was obtained. Hydrogen was added to give a total pressure of 82 bar and the autoclave heated to 80° C. The rate of reaction was 3.05 mol kg$^{-1}$h$^{-1}$ with an overall conversion to triethylammoniun formate of 54.5%, which was separated from the reaction mixture as described in Example 1.

EXAMPLES 3 TO 8

Into the autoclave used for Example 1 were charged 14.1 g triethylamine, 42.2 g isopropanol, 18.6 g water and a series of ruthenium catalysts, see Table 1. In each case the triethylamine and ruthenium catalyst dissolved in the isopropanol/water mixture.

The reactions were carried out at a $CO_2$ pressure of 27 bar with hydrogen added to give a total pressure of 54 bar and at a reaction temperature of 80° C. The rate of reaction and conversion to triethylammonium formate (which was separated from the reaction mixture as described in Example 1) are shown in Table 1.

TABLE 1

| Example No | Catalyst | m moles of catalyst | Length of Reaction h | Rate of Reaction mol kg$^{-1}$h$^{-1}$ | Conversion % |
|---|---|---|---|---|---|
| 3 | $[(p\text{-cym})RuCl_2]_2$ | 0.151 | 3.5 | 0.12 | 14.0 |
| 4 | $[(hmb)RuCl_2]_2$ | 0.150 | 3 | 0.11 | 15.1 |
| 5 | $[(hmb)Ru_2(OH)_3]Cl$ | 0.178 | 5 | 0.11 | 17.8 |
| 6 | $[(hmb)Ru_2(OH)_3]PF_6$ | 0.151 | 16 | 0.08 | 15.5 |
| 7 | $[Ru_3O(OAc)_6(H_2O)]OAc$ | 0.148 | 5 | 0.08 | 9.4 |
| 8 | $[Ru(CO)_2I_2]_n$ | 0.150 | 9 | 0.18 | 26.7 |

P-cym = p-cymene; hmb = hexamethylbenzene
h = hours
kg = kilograms

EXAMPLES 9–14

Into the autoclave used for Example 2 were charged 120.8 g of an isopropanol-water mixture with the percent molar proportion shown in Table 2, 28.2 g triethylamine and 0.137 g $[Ru(CO)_2Cl_2]_n$. The reactions were carried out at initial gas pressures of 27 bar $CO_2$ and 54 bar $H_2$ at a temperature of 80° C.

The rate of reaction and conversion to triethylammonium formate (which was separated as described in Example 1) are shown in Table 2.

TABLE 2

| Example No | % Molar Isopropanol | Proportions Water | Rate of Reaction mol kg$^{-1}$h$^{-1}$ | Conversion % |
|---|---|---|---|---|
| 9 | 0 | 100 | 0.03 | 13.0 |
| 10 | 20 | 80 | 1.47 | 54.5 |
| 11 | 40 | 60 | 2.75 | 59.0 |
| 12 | 60 | 40 | 3.20 | 60.7 |
| 13 | 80 | 20 | 2.90 | 53.2 |
| 14 | 100 | 0 | 0.55 | 43.4 |

This table illustrates that isopropanol/water mixtures give better rates of reaction than water or isopropanol alone.

EXAMPLES 15–17

Into the autoclave used for Example 2 were charged 28.2 g triethylamine, 81.8 g isopropanol, 36.6 g water and 0.137 g $[Ru(CO)_2Cl_2]_n$. After obtaining a steady pressure of carbon dioxide at 27 bar, hydrogen was introduced into the system at various pressures as shown in Table 3. The reactions were carried out at 80° C.

The rate of reaction and conversion to triethylammonium formate which was separated from the reaction mixture as described in Example 1 are shown in Table 3.

TABLE 3

| Example No | Initial Pressure of $H_2$ bar | Rate of Reaction mol kg$^{-1}$h$^{-1}$ | Conversion |
|---|---|---|---|
| 15 | 27.2 | 1.05 | 23.2 |
| 16 | 54.4 | 3.20 | 67.1 |
| 17 | 81.6 | 5.30 | 85.3 |

The results in this table illustrate that increasing the hydrogen partial pressure increases both rate of reaction and conversion.

EXAMPLE 18

Into the autoclave used for Example 2 were charged 40.2 g of a 40% w/w aqueous solution of trimethylamine, 100.0 g isopropanol and 0.137 g [Ru(CO)$_2$Cl$_2$]$_n$. The autoclave was closed and carbon dioxide was introduced until a steady pressure of 27 bar was obtained. Hydrogen was added to give a total pressure of 82 bar and the autoclave heated to 80° C.

The rate of reaction was 0.02 mol kg$^{-1}$h$^{-1}$ with an overall conversion to trimethyl ammonium formate (separated as described in Example 1) of 59.5%.

EXAMPLE 19

Into the autoclave used for Example 2 were charged 21.5 g 1,8-Diazobicyclo (5.4.0)undec-7-ene, 101.2 g isopropanol, 19.6 g water and 0.137 g [Ru(CO)$_2$Cl$_2$]$_n$. The autoclave was closed and carbon dioxide was introduced until a steady pressure of 27 bar was obtained. Hydrogen was added to give a total pressure of 82 bar and the autoclave heated to 80° C.

The rate of reaction was 0.01 mol kg$^{-1}$h$^{-1}$ with an overall conversion to the formate salt (separated as described in Example 1) of 24.8%.

EXAMPLE 20

Into the autoclave used for Example 1 were charged 42.2 g isopropanol, 18.5 g water, 7.8 g 1,4-diazobicyclo(2.2.2)octane and 0.093 g [(p-cymene)RuCl$_2$]$_2$. The autoclave was closed and carbon dioxide was introduced until a steady pressure of 27 bar was obtained. Hydrogen was added to give a total pressure of 54 bar and the autoclave was heated to 80° C.

The rate of reaction was 0.18 mol kg$^{-1}$h$^{-1}$ with an overall conversion to the formate salt (separated as described in Example 1) of 18.0%.

EXAMPLES 21-24

Into the autoclave used for Example 2 were charged 125 g of methanol-water mixture with the percent molar proportions shown in the Table 4 below, 28.2 g of triethylamine and 0.137 g of [Ru(CO)$_2$Cl$_2$]$_n$. The reactions were carried out at initial gas pressures of 27 bar CO$_2$ and 54 bar H$_2$ at a temperature of 80° C.

TABLE 4

| % molar proportion | | Rate of Reaction | Conversion |
|---|---|---|---|
| methanol | water | mole kg$^{-1}$h$^{-1}$ | % |
| 100 | 0 | 0.5 | 19.0 |
| 96 | 4 | 1.8 | 28.5 |
| 88 | 12 | 1.9 | 56.0 |
| 69 | 31 | 2.2 | 63.0 |

The formate salt was separated from the reaction mixture as described in Example 1.

We claim:

1. A process for the production of a formate salt of a nitrogenous base containing a tertiary nitrogen atom which process comprises reacting hydrogen and carbon dioxide with the nitrogenous base, in the presence of a solvent and as catalyst a soluble compound of a transition metal of Group VIII of the Periodic Table according to Mendeleef and separating the formate salt of the base from the reaction mixture.

2. A process as claimed in claim 1 wherein the solvent is an alcohol.

3. A process as claimed in claim 2 wherein the alcohol is a secondary alcohol.

4. A process as claimed in claim 3 wherein the secondary alcohol is isopropanol.

5. A process as claimed in claim 2 wherein the solvent is a mixture of an alcohol and water.

6. A process as claimed in claim 5 wherein the mixture of alcohol and water contains from 30 to 90 mole percent of the alcohol.

7. A process as claimed in claim 1 wherein the Group VIII metal is a noble metal.

8. A process as claimed in claim 7 wherein the noble metal is ruthenium.

9. A process as claimed in claim 1 wherein the process is effected at a temperature from 20° to 200° C. under conditions to maintain the solvent in the liquid phase and the catalyst in solution.

10. A process as claimed in claim 1 wherein the formate salt of the base is separated from the reaction mixture by distillation.

11. A process as claimed in claim 1 wherein the partial pressure of hydrogen in relation to the partial pressure of carbon dioxide is at least 1.5:1.

12. A process as claimed in claim 1 wherein the solvent is a mixture of water and a secondary alcohol, said mixture containing from 30 to 90 mole percent of the secondary alcohol.

13. A process as claimed in claim 12 wherein the solvent mixture contains from 50 to 70 mole percent of the secondary alcohol.

14. A process as claimed in claim 13 wherein the secondary alcohol is isopropanol.

15. A process as claimed in claim 1 wherein the solvent is a mixture of water and methanol, said mixture containing from 30 to 90 mole percent of the methanol.

16. A process as claimed in claim 15 wherein the solvent mixture contains from 69 to 88 mole percent of the methanol.

17. A process as claimed in claim 1 wherein the partial pressure of hydrogen in relation to the partial pressure of carbon dioxide is from about 2:1 to about 3:1.

* * * * *